(12) United States Patent  
Tucek et al.

(10) Patent No.: US 7,118,588 B2
(45) Date of Patent: Oct. 10, 2006

(54) SCANNING TREATMENT LASER

(76) Inventors: Kevin Tucek, 3960 E. Palm La. Bldg. 9, Mesa, AZ (US) 85215; Steven C. Shanks, 3960 E. Palm La. Bldg. 9, Mesa, AZ (US) 85215

( * ) Notice: Subject to any disclaimer, the term of this patent is extended or adjusted under 35 U.S.C. 154(b) by 0 days.

(21) Appl. No.: 10/772,738

(22) Filed: Feb. 4, 2004

(65) Prior Publication Data

US 2004/0158301 A1    Aug. 12, 2004

Related U.S. Application Data

(63) Continuation-in-part of application No. 09/932,907, filed on Aug. 20, 2001, now Pat. No. 6,746,473.

(60) Provisional application No. 60/273,282, filed on Mar. 2, 2001.

(51) Int. Cl.
*A61N 5/67* (2006.01)

(52) U.S. Cl. ............................... 607/89; 606/9; 607/88

(58) Field of Classification Search ............ 607/88–89; 606/9; 359/196–220
See application file for complete search history.

(56) References Cited

U.S. PATENT DOCUMENTS

| | | | | |
|---|---|---|---|---|
| 2,987,960 A | * | 6/1961 | Sheldon | 359/367 |
| 3,023,662 A | * | 3/1962 | Hicks Jr. | 359/220 |
| 3,966,319 A | * | 6/1976 | Lang | 355/66 |
| 4,001,840 A | * | 1/1977 | Becker et al. | 347/259 |
| 4,176,925 A | * | 12/1979 | Kocher et al. | 396/547 |
| 4,984,892 A | * | 1/1991 | Hofmann | 356/625 |
| 5,151,815 A | * | 9/1992 | Baillet | 359/220 |
| 5,252,816 A | * | 10/1993 | Onimaru et al. | 235/462.36 |
| 5,336,217 A | * | 8/1994 | Buys et al. | 606/9 |
| 5,422,471 A | * | 6/1995 | Plesko | 235/462.36 |
| 5,537,214 A | * | 7/1996 | Aiba et al. | 358/296 |
| 5,653,706 A | * | 8/1997 | Zavislan et al. | 606/9 |
| 5,743,902 A | * | 4/1998 | Trost | 606/18 |
| 5,860,967 A | * | 1/1999 | Zavislan et al. | 606/9 |
| 5,879,376 A | * | 3/1999 | Miller | 607/89 |
| 5,971,978 A | * | 10/1999 | Mukai | 606/18 |
| 6,013,096 A | * | 1/2000 | Tucek | 607/89 |
| 6,383,177 B1 | * | 5/2002 | Balle-Petersen et al. | 606/9 |
| 6,626,834 B1 | * | 9/2003 | Dunne et al. | 600/444 |
| 6,641,578 B1 | * | 11/2003 | Mukai | 606/9 |
| 6,900,916 B1 | * | 5/2005 | Okazaki et al. | 359/202 |
| 2002/0138071 A1 | * | 9/2002 | Angeley et al. | 606/9 |
| 2002/0138119 A1 | * | 9/2002 | Angeley et al. | 607/88 |
| 2004/0030368 A1 | * | 2/2004 | Kemeny et al. | 607/88 |
| 2004/0212863 A1 | * | 10/2004 | Schanz et al. | 359/211 |
| 2005/0033388 A1 | * | 2/2005 | Brugger et al. | 607/89 |

* cited by examiner

*Primary Examiner*—Henry M. Johnson, III
(74) *Attorney, Agent, or Firm*—Sandra L Etherton; Etherton Law Group, LLC

(57) ABSTRACT

An therapeutic laser device that incorporates a scanning head to direct low level laser light into a treatment zone that can have any desired shape or energy distribution within a hemisphere forward of the scanning head. The device enables laser light of different pulse widths, different beam shapes and different energy distributions to be applied externally to a patient's body.

2 Claims, 4 Drawing Sheets

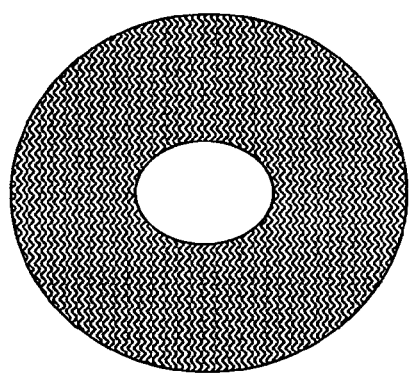
FIG. 3a
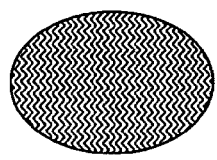
FIG. 3b
FIG. 3c
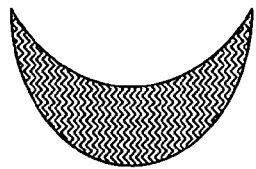
FIG. 3d
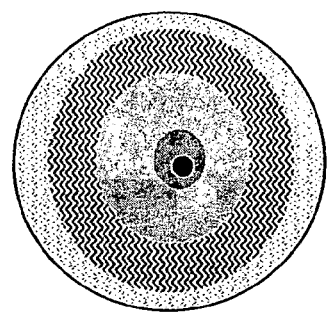
FIG. 3e
FIG. 3f

SCANNING TREATMENT LASER

CROSS-REFERENCE TO RELATED APPLICATIONS

This application is a continuation-in-part of U.S. patent application Ser. No. 09/932,907, now U.S. Pat. No. 6,746,473, filed on Aug. 20, 2001, which claims the benefit of U.S. Provisional Application No. 60/273,282 filed Mar. 2, 2001.

FIELD OF INVENTION

This invention relates generally to medical devices that employ lasers. More particularly, this Invention relates to a treatment laser device that incorporates a scanning head to deliver a beam spot of any shape.

BACKGROUND

Low level laser therapy (LLLT) utilizes low level laser energy in the treatment of a broad range of conditions. LLLT improves wound healing, reduces edema, and relieves pain of various etiologies, including successful application post-operatively to liposuction to reduce inflammation and pain. LLLT is also used during liposuction procedures to facilitate removal of fat by causing intracellular fat to be released into the interstice. It is also used in the treatment and repair of injured muscles and tendons.

The LLLT treatment has an energy dose rate that causes no immediate detectable temperature rise of the treated tissue and no macroscopically visible changes in tissue structure. Consequently, the treated and surrounding tissue is not heated and is not damaged. There are a number of variables in laser therapy including the wavelength of the laser beam, the area impinged by the laser beam, laser energy, pulse width, treatment duration and tissue characteristics. The success of each therapy depends on the relationship and combination of these variables. For example, liposuction may be facilitated with one regimen utilizing a given wavelength and treatment duration, whereas pain may be treated with a regimen utilizing a different wavelength and treatment duration, and inflammation a third regimen. Specific devices are known in the art for each type of therapy.

An earlier patent, U. S. Pat. No. 6,013,096, describes a hand-held wand that houses a red semiconductor laser and optics to deliver the beam from the laser to the skin of a patient. A simple timing circuit is provided for controlling the length of time a laser beam is emitted from the wand. An optical arrangement causes the emitted light to form a line on the patient's skin, the shape of the light as it impinges the patient's skin referred to herein as the beam spot.

Reference may also be had to our co-pending application Ser. No. 09/932,907 which describes a device that delivers two or more laser beams with different characteristics to treat a patient for multiple types of problems during a single treatment. The patent application describes a hand-held wand that houses a plurality of laser energy sources and optics to direct laser beams from the sources to a patient. Control electronics are provided to vary such parameters as the pulse repetition rate. Optics are also provided to select the beam shape of the laser output, which in turn determines the beam spot.

Both of these devices rely on a static optical arrangement to produce a beam spot. Neither of the devices provides a means for varying the shape of the beam spot on demand nor for automatically varying the resultant intensity. It has become clear in LLLT that there is benefit in being able to customize the delivery of the laser light treatment by changing the shape and energy distribution of the delivered beam spot.

Therefore, an object of this invention is to provide a laser therapy device that enables shaping of the delivered laser beam to suit multiple types of treatments. It is a particular object of this invention to provide a hand-held therapeutic laser device to provide low level laser therapy which can be used to treat injured muscles and tendons, facilitate liposuction, and treat post-operative inflammation and pain.

SUMMARY OF THE INVENTION

This invention is an improved laser device that can deliver a desired beam spot to a treatment area and to provide multiple types of low level laser therapy treatments. The device enables laser light of any beam spot and intensity to be applied externally to a patient's body. The device utilizes a means for causing the laser to scan rapidly and may include multiple laser sources.

BRIEF DESCRIPTION OF THE DRAWINGS

FIG. 3 shows examples of shapes achievable with the present invention.

DETAILED DESCRIPTION OF THE INVENTION

Figure 1:
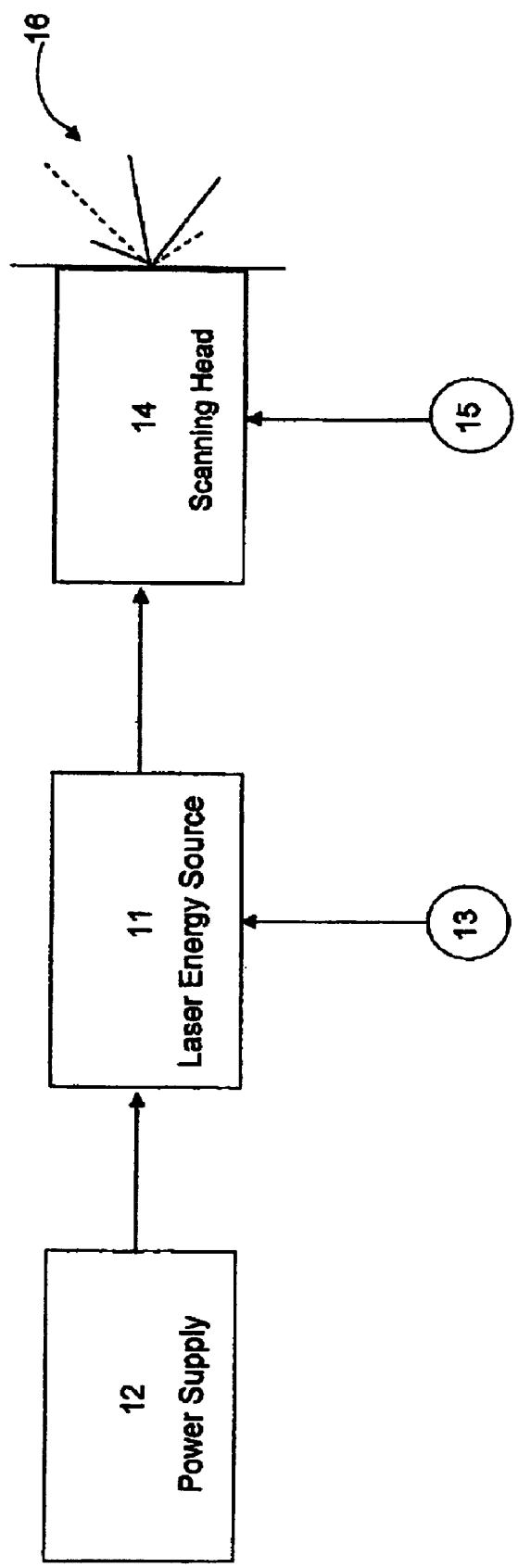
FIG. 1 is a schematic illustration of a preferred embodiment of the present invention.

Referring to the drawings, there is illustrated a schematic of a hand-held laser device. The device includes at least one laser energy source 11, a power source 12, a laser control 13, a scanning head 14, and a scanner control 15. FIG. 1 shows the preferred embodiment in which a laser energy source 11 is connected to a power source 12. The power source preferably provides direct current, such as that provided by a battery, but may instead provide alternating current such as that provided by conventional building outlet power (120V) that is then converted to direct current. The power source 12 may be housed in the wand or may be deployed separately with an electrical cable joining it to the wand. A laser control 13 is connected to the laser energy source 11 acts as an on/off switch to control the period of time the laser light is generated. Other functions of the laser control 13 are mentioned below.

A scanning mechanism directs the laser beam emitted from the laser source 11 to any position on the patient. In the preferred embodiment, the laser beam emitted from the laser source 11 is directed to the scanning head 14 which deflects the laser beam into any position within a hemisphere in front of the scanning head, as depicted by the lines 16. With electronic or computerized control, the scanning head is able to automatically move very quickly, causing the laser beam to appear to create any static shape on the patient's skin. The static shape, however, is actually the result of the scanning light moving from location to location at a speed that makes the motion nearly imperceptible to the human eye. In this way any desired shape of light can be achieved, regardless of the actual cross-sectional shape of the laser beam. If the laser is directed to scan across one area more than another, the intensity of the laser therapy is greater in the area of high scan.

Figure 2:
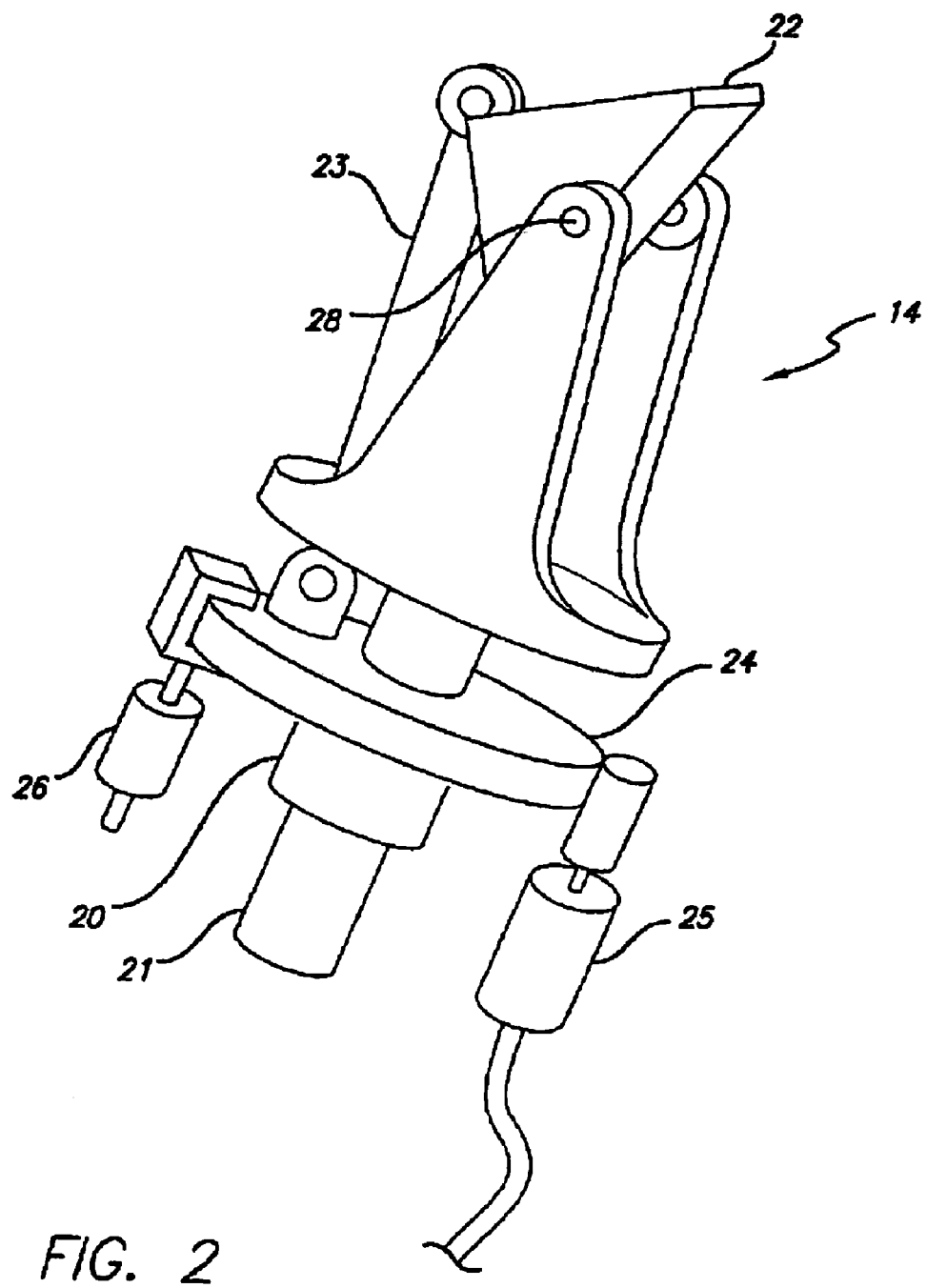
FIG. 2 is a side view of a scanning head of the preferred embodiment of FIG. 1.

A preferred structure for the scanning head 14 is shown in FIG. 2. The scanning head comprises a hollow spindle 20 mounted on a hollow shaft 21. The laser beam passes through the hollow shaft 21 and strikes an optical element 22 which deflects the laser beam into a desired location. Although the optical element is shown as a prism in the preferred embodiment it will be appreciated that a mirror could also be used. The optical element, referred to hereinafter as prism 22, is mounted on a transverse axle 28 so that it can rotate through at least 180 degrees. In some applications a lesser degree of travel may be sufficient. The position of the prism 22 is controlled by a hinged drive arm 23 connected to the prism at one end and a cam 24 at the other end. The cam 24 is able to travel along the spindle 20 thus causing rotation of the prism 22. Furthermore, the spindle 20 is able to rotate on the shaft 21. The combination of the rotation of the spindle 20 and movement of the cam 24 positions the prism so as to direct the laser beam into any position within a hemisphere in front of the scanning head.

The position of the prism may be controlled by micromanipulators according to signals received from the scanner control 15. Any suitable mechanism may be employed but in the preferred embodiment a motor 25 rotates the cam 24 and a solenoid 26 extends (retracts) the cam longitudinally. The combination of rotation and extension of the cam controls the position of the prism or mirror. It will be appreciated that both these functions could be provided by a single micromanipulator acting on the cam 24.

While the preferred embodiment utilizes the scanning head 14, other mechanisms for causing laser scan may be used, such as raster scanners like galvanometers, rotating mirrors, speaker scanners; also diffraction grating rotators, light diffusers and the electronics necessary to generate and control image patterns.

The scanner control 15 is programmed to move the scanning head 14 in a required manner to achieve any desired shape of a treatment zone on the skin of a patient. A sample selection of available shapes is shown in FIG. 3. It will be appreciated that the range of available shapes are not limited to those shown in FIG. 3.

Furthermore, the scanner control 15 can be programmed to direct the laser output into some regions more than others so that one region may have greater treatment than another region. For example, a donut shaped beam may be produced with less energy delivered to the edges of the donut (an example is shown in FIG. 3). In this manner the precise energy distribution can be obtained for any given treatment regime.

Persons skilled in the art will be aware that various laser energy sources are known in the art for use in low-level laser therapy. They include Helium-Neon lasers having a 632 nm wavelength and semiconductor diode lasers with a broad range of wavelengths between 600–800 nm. The laser energy source in the preferred embodiment is a semiconductor laser diode that produces light in the red range of the visible spectrum, having a wavelength of about 635 nm. Other suitable wavelengths are used for other particular applications.

The preferred embodiment is described as having a single laser energy source 11 but it will be appreciated that the invention may have two or more laser energy sources. While many LLLT regimen include ultraviolet or infrared laser light, it is advantageous to utilize at least one laser beam in the visible energy spectrum so that the operator can see the laser light as it impinges the patent's body and the area treated can be easily defined.

Different therapy regimens require diodes of different wattages. The preferred laser diodes use less than one watt of power each to simultaneously facilitate liposuction, treat post-operative inflammation, and post-operative pain. Diodes of various other wattages may also be employed to achieve the desired laser energy for the given regimen. However, higher power lasers require a larger power source which to some extent negates the ease of handling of the hand-held wand shown in FIG. 4. It may be advantageous to provide a power source separate from the wand, and deliver the power to the wand by wire. An advantage of the present invention is that a larger treatment area can be achieved without the need for a higher power laser. Furthermore, by careful choice of beam shape, the available laser light can be used more efficiently than is achievable with the prior art LLLT devices.

Laser control 13 also forms a control circuit that controls the duration of each pulse of laser light emitted and the repetition rate. When there are no pulses, a continuous beam of laser light is generated. Repetition rates from 0 to 100,000 Hz may be employed to achieve the desired effect on the patient's tissue. The goal for LLLT regimen is to deliver laser energy to the target tissue utilizing a pulse width short enough to sufficiently energize the targeted tissue and avoid thermal damage to adjacent tissue.

Figure 4:
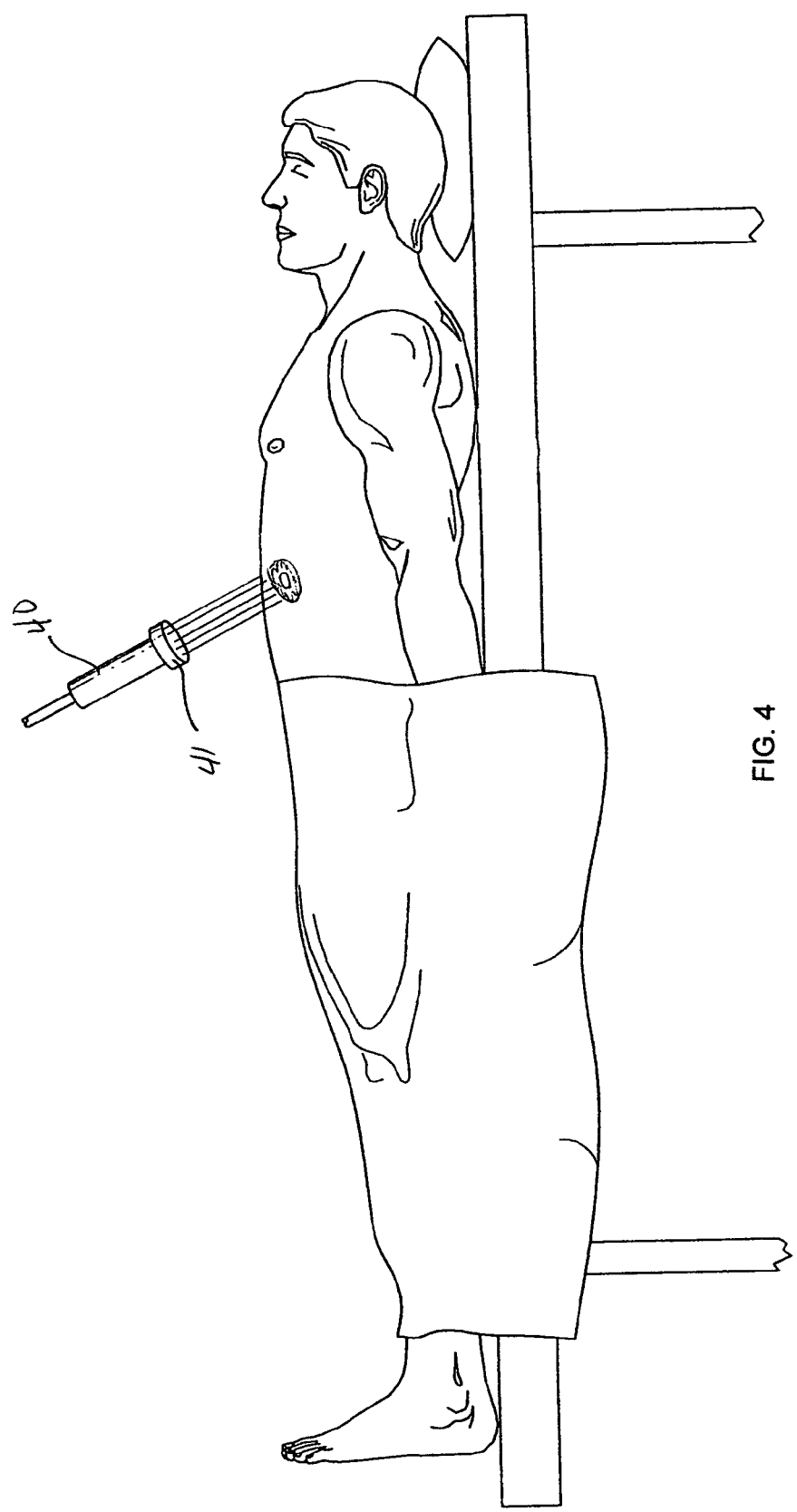
FIG. 4 is a schematic illustration of application of low-level laser radiation using the preferred embodiment of the present invention.

In order to direct the laser light to the desired area on a patient, the laser light is emitted from a lightweight, hand-held pointer referred to herein as a wand 40. As shown in FIG. 4. The wand 40 is an elongated hollow tube defining an interior cavity which is shaped to be easily retained in a user's hand. In the preferred embodiment the laser energy source 11 is mounted in the wand's interior cavity, although the laser energy source could be remotely located and the laser light conducted by fiber optics to the wand. The wand may take on any shape that enables the laser light to be directed as needed such as tubular, T-shaped, substantially spherical, or rectangular. As mentioned above, the wand may contain the power supply (for example a battery) or the power supply may be remote with power supplied by an electrical cable. The scanning head 14 may be contained wholly within the wand 40 or may be contained within a separate fitting 41 that attaches to the end of the wand, as shown in FIG. 4.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

We claim:

1. A laser device comprising:
   a) at least one laser energy source for generating a laser beam;
   b) a wand from which the laser beam emits, the wand being capable of being retained in a hand of a user and freely moved relative to the surface of the skin of a patient; and
   c) a scanning head attached to the wand for receiving the laser beam and for directing the laser beam to a desired location wherein the scanning head comprises a spindle mounted for rotation on a hollow shaft, an optical element mounted on the spindle and rotatable in a plane perpendicular to a plane of rotation of the spindle, a cam slidably mounted on the spindle and rotatable with the spindle, and a hinged arm joining the cam to the optical element such that sliding motion of the cam on the spindle causes rotation of the single optical element relative to the spindle.

2. A therapeutic laser device comprising:

a) a laser energy source generating a laser beam;

b) a wand from which the laser beams emit, the wand having an interior cavity and being capable of being retained in the hand of a user and freely moved relative to the surface of the skin of the patient;

c) a scanning head mounted in the interior cavity of the wand for receiving the laser beam and for directing the laser beam into a desired location, the scanning head comprising a spindle mounted for rotation on a hollow shaft, an optical element mounted on the spindle and rotatable in a plane perpendicular to the plane of rotation with the spindle, a cam slidably mounted on the spindle and rotatable with the spindle, and a hinged arm joining the cam to the optical element such that sliding motion of the cam on the spindle causes rotation of the optical element relative to the spindle; and d) a control circuit for controlling the scanning head to direct the laser beam to form a desired shape.

* * * * *